(12) United States Patent
Kankan et al.

(10) Patent No.: US 7,973,173 B2
(45) Date of Patent: Jul. 5, 2011

(54) PROCESS FOR THE SYNTHESIS OF AN ACE INHIBITOR

(75) Inventors: Rajendra Narayanrao Kankan, Maharashtra (IN); Dharmaraj Ramachandra Rao, Maharashtra (IN); Manjinder Singh Phull, Maharashtra (IN); Ashwini Sawant, Maharashtra (IN); Dilip Ramdas Birari, Maharashtra (IN)

(73) Assignee: Cipla Limited, Mumbai (IN)

( * ) Notice: Subject to any disclaimer, the term of this patent is extended or adjusted under 35 U.S.C. 154(b) by 389 days.

(21) Appl. No.: 11/993,858

(22) PCT Filed: Jul. 5, 2006

(86) PCT No.: PCT/GB2006/002496
§ 371 (c)(1),
(2), (4) Date: Mar. 27, 2008

(87) PCT Pub. No.: WO2007/003947
PCT Pub. Date: Jan. 11, 2007

(65) Prior Publication Data
US 2009/0069574 A1   Mar. 12, 2009

(30) Foreign Application Priority Data
Jul. 5, 2005 (IN) .......................... 793/MUM/2005

(51) Int. Cl.
*C07D 209/42* (2006.01)
(52) U.S. Cl. ...................................... 548/452
(58) Field of Classification Search ............ 548/452
See application file for complete search history.

(56) References Cited

U.S. PATENT DOCUMENTS

| | | | |
|---|---|---|---|
| 3,901,915 A * | 8/1975 | Perry et al. | 548/498 |
| 4,490,386 A | 12/1984 | Seamans et al. | |
| 4,496,541 A | 1/1985 | Huang et al. | |
| 4,933,361 A | 6/1990 | Urbach et al. | |
| 5,359,086 A | 10/1994 | Merslavic et al. | |
| 6,559,318 B1 | 5/2003 | Ebel et al. | |
| 2006/0079698 A1 * | 4/2006 | Joshi et al. | 548/492 |

FOREIGN PATENT DOCUMENTS

| | | |
|---|---|---|
| EP | 0088341 A1 | 9/1983 |
| EP | 0215335 A2 | 3/1987 |
| EP | 1197490 A1 | 4/2002 |
| JP | 57175152 | 10/1982 |
| WO | 8601803 A1 | 3/1986 |
| WO | 9633984 A1 | 10/1996 |
| WO | 0040555 A1 | 7/2000 |
| WO | 2004065368 A1 | 8/2004 |
| WO | 2005051909 A1 | 6/2005 |
| WO | 2005054194 A1 | 6/2005 |
| WO | 2007003947 A2 | 1/2007 |
| WO | 2007003947 A3 | 1/2007 |

OTHER PUBLICATIONS

Handbook of Reagents for Organic Synthesis Chiral Reagents for Asymmetric Synthesis, L.A. Paquette (Ed.), 2003, John Wiley & Sons Ltd., pp. 406-410 (Chapter 13), and 585 & 586 (Index).*
Foreign communication from a related counterpart application— International Preliminary Report on Patentability, PCT/ GB2006/ 002496, Oct. 19, 2007, 10 pages.
Foreign communication from a related counterpart application— International Search Report and Written Opinion, PCT/ GB 2006/ 002496, Mar. 14, 2007, 14 pages.
Suh, John T., et al., "Angiotensin-converting enzyme inhibitors: N-substituted glycine derivatives," XP-001106728, 1985, pp. 563-570, vol. 20, No. 6, Eur. J. Med. Chem.

* cited by examiner

*Primary Examiner* — Jason M Nolan
(74) *Attorney, Agent, or Firm* — Conley Rose, P.C.; Rodney B. Carroll

(57) ABSTRACT

A process for the synthesis of trandolapril which comprises condensing N—[I—(S)-ethoxycarbonyl-3-phenylpropyl]-L-alanine N-carboxyanhydride with trans octahydro-1H-indole-2-carboxylic acid in a first organic solvent comprising a water immiscible inert organic solvent and in the presence of a base, and isolating trandolapril from a second organic solvent. N-[1-(S)-ethoxycarbonyl-3-phenylpropyl]-L-alanine N-carboxyanhydride may also be condensed with (2S,3aR,7aS) octahydro-1H-indole-2-carboxylic acid in a first organic solvent and in the presence of a base, and trandolapril isolated. There is also provided a process for the resolution of racemic trans octahydro-1H-indole-2-carboxylc acid.

14 Claims, No Drawings

PROCESS FOR THE SYNTHESIS OF AN ACE INHIBITOR

TECHNICAL FIELD OF THE INVENTION

The present invention relates to an improved, simple and efficient process for the synthesis and isolation of (2S,3aR,7aS)-1-[(2S)-2-[[(1S)-1-ethoxycarbonyl-3-phenylpropyl]amino]-1-oxopropyl]octahydro-1H-indole-2-carboxylic acid. i.e. trandolapril, a compound of formula (I).

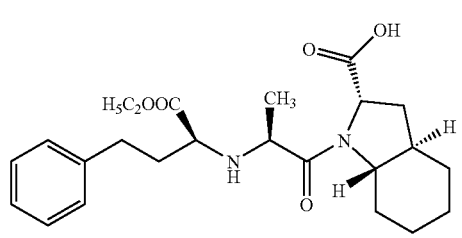

BACKGROUND OF THE INVENTION

Trandolapril, a compound of formula (I), is chemically described as (2S,3aR,7aS)-1-[(2S)-2-[[(1S)-1-ethoxycarbonyl-3-phenylpropyl]amino]-1-oxopropyl]octahydro-1H-indole-2-carboxylic acid. Trandolapril is the ethyl ester prodrug of a nonsulfhydryl angiotensin converting enzyme (ACE) inhibitor, trandolaprilat.

Trandolapril is a drug that is used to lower blood pressure. Blood pressure is dependent on the degree of constriction (narrowing) of the arteries and veins. The narrower the arteries and veins, the higher the blood pressure. Angiotensin II is a chemical substance made in the body that causes the muscles in the walls of arteries and veins to contract, narrowing the arteries and veins and thereby elevating blood pressure. Angiotensin II is formed by an enzyme called angiotensin converting enzyme (ACE). Trandolapril is an inhibitor of ACE and blocks the formation of angiotensin II thereby lowering blood pressure. The drop in blood pressure also means that the heart does not have to work as hard because the pressure it must pump blood against is less. The efficiency of a failing heart improves, and the output of blood from the heart increases. Thus, ACE inhibitors such as trandolapril are useful in treating heart failure.

Trandolapril's ACE-inhibiting activity is primarily due to its diacid metabolite, trandolaprilat, which is approximately eight times more active as an inhibitor of ACE activity.

Trandolapril along with other related compounds was first disclosed in U.S. Pat. No. 4,933,361. The process for the synthesis of trandolapril was described in U.S. Pat. No. 4,933,361 and WO9633984.

U.S. Pat. No. 4,933,361 describes a process for the synthesis of trandolapril wherein the racemic benzyl ester of octahydro indole-2-carboxylic acid is reacted with N-[1-(S)-ethoxy carbonyl-3-phenyl propyl]-L-alanine (ECPPA), to get racemic benzyl trandolapril, which is purified using column chromatography to get the 2S isomer of benzyl trandolapril, which is further debenzylated with Pd on carbon to get trandolapril as a foamy solid. This process has certain disadvantages, for example the product is obtained in very low yield. Purification is done using column chromatography, which is not suitable for industrial scale up.

WO9633984 discloses a process in which N-[1-(S)-ethoxy carbonyl-3-phenyl propyl]-L-alanine is activated with N-chlorosulfinyl imidazole, to get (N-[1-(S)N-[1-(S)-ethoxy carbonyl-3-phenyl propyl]-L-alanyl-N-sulfonyl anhydride and which is further reacted with silyl-protected 2S,3aR,7aS octahydro indole 2-carboxylic acid to obtain trandolapril. The main disadvantages of this process are that the silyl-protected intermediates are very sensitive to moisture, the process requires anhydrous conditions to be maintained and the solvent used has to be completely dried. It is very difficult to maintain such conditions on an industrial scale, and failing to do so leads to low yield of product.

The processes for preparing N-[1-(S)-ethoxy carbonyl-3-phenyl propyl]-L-alanine N-carboxyanhydride which is used in the process of the present invention are well known and are disclosed in JP57175152A, U.S. Pat. No. 4,496,541, EP215335, U.S. Pat. No. 5,359,086 and EP1197490B1.

Trans octahydro-1H-indole-2-carboxylic acid and its esters are the key intermediates in the synthesis of trandolapril. When synthesized, trans octahydro-1H-indole-2-carboxylic acid is a mixture of four isomers, as shown below.

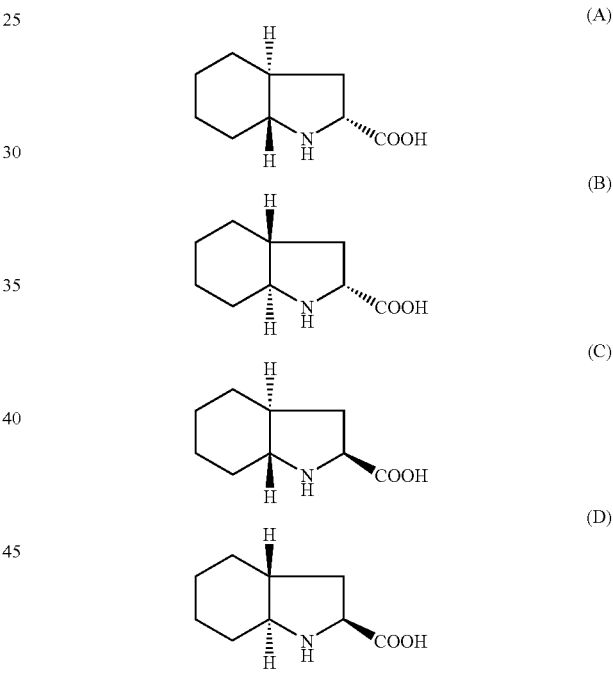

From the processes known in the prior art, trans octahydro-1H-indole-2-carboxylic acid is converted to its ester and the ester is then either reacted directly with N-[1-(S)-ethoxy carbonyl-3-phenyl propyl]-L-alanine (ECPPA) and then the isomers are separated by column chromatography, or alternatively the ester is reacted with ECPPA followed by deprotection. Trans octahydro-1H-indole-2-carboxylic acid is always used in its protected form. No attempts have been made to resolve free trans octahydro-1H-indole-2-carboxylic acid to convert it to the desired isomer (isomer D, above). Furthermore, none of the prior art processes is stereoselective, so resolution of the required isomer is required following condensation.

EP0088341 and U.S. Pat. No. 4,490,386 describe a method for the resolution of N-benzoyl (2RS,3aR,7aS) octahydro-1H-indole-2-carboxylic acid using α-phenyl ethyl amine.

U.S. Pat. No. 6,559,318 and EP1140826 describe a process for the synthesis of (2S,3aR,7aS) octahydro-1H-indole-2-carboxylic acid using enzymatic resolution of its nitrile intermediate. Enzymatic resolution involves many steps and also requires column chromatography for purification making the process uneconomical industrially.

WO8601803 describes the preparation of (2S,3aR,7aS) octahydro-1H-indole-2-carboxylic acid ethyl ester and benzyl ester using 10-D-camphor sulphonic acid.

WO2004065368 describes the synthesis of (2S,3aR,7aS) octahydro-1H-indole-2-carboxylic acid benzyl ester by resolution using 10-D-camphor sulphonic acid to prepare trandolapril. This process gives poor yields because the product has to be first resolved and then the ester is deprotected leading to further loss in yield, making the process low yielding and expensive.

WO2005/051909 describes a process for the preparation of trandolapril, i.e. {N-[1-(S)-carbethoxy-3-phenylpropyl]-S-alanyl-2S,3aR,7aS-octahydroindol-2-carboxylic acid} as well as its pharmaceutical acceptable salts, using a racemic mixture of trans octahydroindole-2-carboxylic acid with the N-carboxyanhydride of {N-[1-(S)-ethoxycarbonyl-3-phenylpropyl}-S-alanyl (NCA) in a molar ratio of 1:1 to 1.6:1 in a mixture of water and water-miscible solvent to obtain a mixture of diastereomers of trandolapril. The diastereomers are converted to salts which upon repeated crystallization from acetone and water, and reaction with a base gives pure trandolapril. Thus, the condensation reaction in the presence of water and a water-miscible solvent is not stereoselective.

The processes for preparing N-[1-(S)-ethoxy carbonyl-3-phenyl propyl]-L-alanine N-carboxyanhydride starting from N-[1-(S)-ethoxy carbonyl-3-phenyl propyl]-L-alanine (ECPPA) are well known and are disclosed in JP57175152A, U.S. Pat. No. 4,496,541, EP215335, U.S. Pat. No. 5,359,086 and EP1197490B1.

The processes for the synthesis of trandolapril described in the prior art have numerous disadvantages as described above. Hence there is a need for a simple and efficient process for the synthesis of trandolapril. The present invention describes a process, which solves this problem. The present process is neither obvious nor anticipated from any of the processes described in the prior art.

OBJECT OF THE INVENTION

The object of the present invention is to provide an improved process for the synthesis of (2S,3aR,7aS)-1-[(2S)-2-[[(1S)-1-Ethoxycarbonyl-3-phenylpropyl]amino]-1-oxo-propyl]-octahydro-1H-indole-2-carboxylic acid from (2S,3aR,7aS) octahydro-1H-indole-2-carboxylic acid.

Another object is to provide a stereo selective process for preparing trandolapril from racemic trans octahydro-1H-indole-2-carboxylic acid.

A further object is to provide a process for the resolution of (2RS,3aR,7aS) octahydro-1H-indole-2-carboxylic acid.

Yet another objective of the present invention is to provide pharmaceutical compositions comprising trandolapril.

SUMMARY OF THE INVENTION

According to a first aspect of the present invention, there is provided a process for the synthesis of trandolapril of Formula (I)

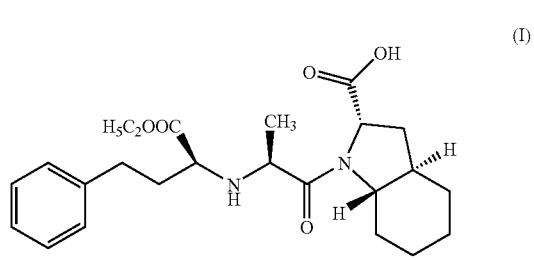

which comprises condensing N-[1-(S)-ethoxycarbonyl-3-phenylpropyl]-L-alanine N-carboxyanhydride compound of formula (II)

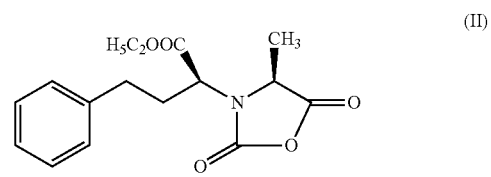

with trans octahydro-1H-indole-2-carboxylic acid of formula (III).

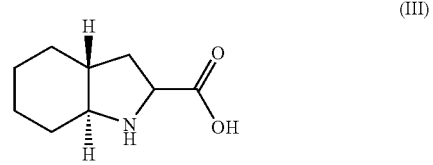

The condensation is preferably carried out in a first organic solvent, suitably comprising a water immiscible inert organic solvent. The condensation may also be carried out in the presence of a base, suitably an organic base. In one embodiment, the base is triethylamine. Trandolapril of formula (I) may be isolated from a second organic solvent.

According to a second aspect of the present invention, there is provided a process for the synthesis of trandolapril of Formula (I) which comprises condensing a compound of formula (II)

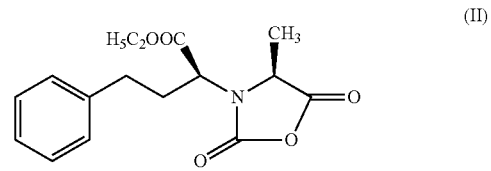

with (2S,3aR,7aS) octahydro-1H-indole-2-carboxylic acid of formula (IV).

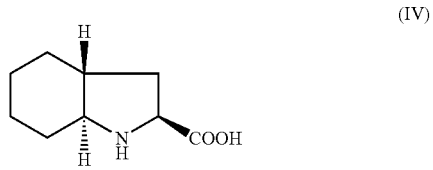

The condensation is preferably carried out in a first organic solvent. The condensation may also be carried out in the presence of a base, suitably an organic base. In one embodiment, the base is triethylamine. Trandolapril of formula (I)

may then be isolated. The trandolapril may be isolated from a second organic solvent. In an embodiment, the first organic solvent is a water immiscible inert organic solvent. In another embodiment, the (2S,3aR,7aS)octahydro-1H-indole-2-carboxylic acid of formula (IV) is prepared by resolution of a compound of formula (III), preferably using R (+) phenyl ethyl amine in a third organic solvent. The third organic solvent may be an alcohol, suitably ethanol.

In a preferred embodiment, the N-[1-(S)-ethoxycarbonyl-3-phenylpropyl]-L-alanine N-carboxyanhydride compound of formula (II) is reacted in a sub-molar proportion relative to the octahydro-1H-indole-2-carboxylic acid of formula (II) or (IV). In an embodiment, the molar ratio of N-[1-(S)-ethoxycarbonyl-3-phenylpropyl]-L-alanine N-carboxyanhydride compound of formula (II) to trans octahydro-1H-indole-2-carboxylic acid of formula (III) is 0.4-0.9:1. In a particularly preferred embodiment, the molar ratio of N-[1-(S)-ethoxycarbonyl-3-phenylpropyl]-L-alanine N-carboxyanhydride compound of formula (II) to trans octahydro-1H-indole-2-carboxylic acid of formula (III) is 0.5-0.8:1.

In an embodiment, the first organic solvent is non-polar. Suitably, the first organic solvent is dichloromethane, dichloroethane, chloroform, toluene, xylene or an organic ester. Preferably, the first organic solvent is dichloromethane.

In another embodiment, the second organic solvent is ethyl acetate, isopropyl acetate, acetone, acetonitrile or isopropyl alcohol, preferably acetonitrile.

In another embodiment, the condensation is carried out at a temperature ranging from 5° C. to ambient temperature, preferably at ambient temperature.

In a further embodiment, the process further comprises quenching the product of the condensation reaction with water. Optionally, the pH of the quenched product may be adjusted to 4 to 7, suitably with an acid. Typically, the pH is adjusted to 4.2. The process may further comprise extracting the pH-adjusted product with a suitable solvent, followed by concentrating the extracted product to a residue. In this embodiment, the second organic solvent is used to isolate trandolapril from the residue.

According to a third aspect of the present invention, there is provided a process for the resolution of racemic trans octahydro-1H-indole-2-carboxylic acid to obtain (2S,3aR,7aS) octahydro-1H-indole-2-carboxylic acid compound of formula (IV), wherein the resolution uses a resolving agent, preferably a R-(+)-phenyl ethyl amine resolving agent. In an embodiment, the resolution is carried out in a solvent, such as an alcohol. Preferably, the solvent is ethanol.

According to another aspect of the present invention, there is provided the use of (2S,3aR,7aS) octahydro-1H-indole-2-carboxylic acid of formula (IV) in a process for preparing trandolapril.

According to a further aspect of the present invention, there is provided trandolapril prepared according to the process of the present invention.

According to a still further aspect of the present invention, there is provided a pharmaceutical composition comprising trandolapril prepared according to the process of the present invention, and a pharmaceutically acceptable carrier.

The term "sub-molar proportion" is used herein to mean in a proportion less than equimolar. In other words, a sub-molar proportion of N-[1-(S)-ethoxy carbonyl-3-phenyl propyl]-L-alanine N-carboxyanhydride relative to trans-octahydro-1H-indole-2-carboxylic acid means the ratio of N-[1-(S)-ethoxy carbonyl-3-phenyl propyl]-L-alanine N-carboxyanhydride to trans-octahydro-1H-indole-2-carboxylic acid would be (less than 1):1. In a preferred embodiment of the present invention, the molar ratio of N-[1-(S)-ethoxy carbonyl-3-phenyl propyl]-L-alanine N-carboxyanhydride to trans-octahydro-1H-indole-2-carboxylic acid is 0.4-0.9:1, more preferably 0.5-0.8:1.

DETAILED DESCRIPTION OF THE INVENTION

The present invention relates to an improved, simple and efficient process for the synthesis of trandolapril, which is ideally suitable for industrial scale-up. The process of the present invention is described in Scheme 1 below

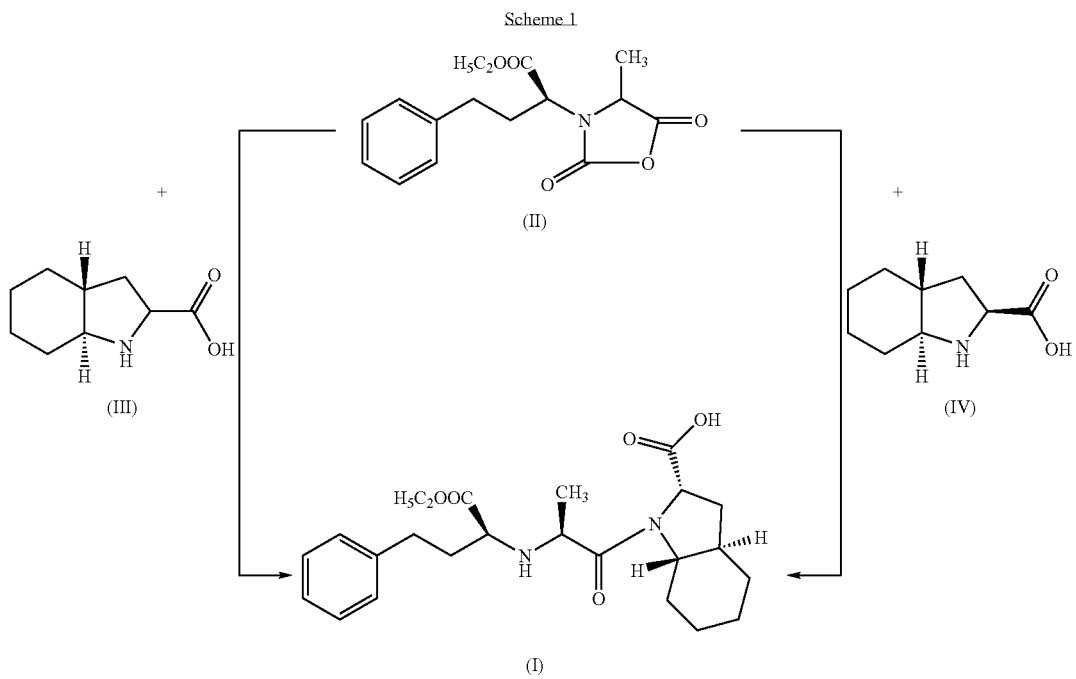

One aspect of the present invention provides a process for the synthesis of trandolapril wherein trans octahydro-1H-indole-2-carboxylic acid (III) is reacted with N-[1-(S)-ethoxy carbonyl-3-phenyl propyl]-L-alanine N-carboxyanhydride (II) (referred herein as NCA) in a suitable organic solvent, preferably a water immiscible inert non polar organic solvent. The organic solvent may be dichloromethane, dichloroethane, chloroform, toluene, xylene or an organic ester. Preferably the organic solvent is dichloromethane. The condensation is carried out in the presence of a base, preferably triethylamine.

The reaction is preferably carried out at a temperature ranging from 5° C. to ambient temperature, more preferably at ambient temperature. As used herein, "ambient temperature" means a temperature in the range of about 25° C. to about 30° C.

The reaction mass may be quenched with water and the pH adjusted to 4-7, preferably to pH 4.2, with an acid. The reaction mass may then be extracted, suitably with dichloromethane, and concentrated to residue. The residue may be dissolved and refluxed in a suitable solvent preferably in ethyl acetate, isopropyl acetate, acetone, acetonitrile, isopropyl alcohol, more preferably acetonitrile. The product is isolated by cooling the reaction mass to room temperature and filtering the resulting solid.

Another aspect of the present invention provides a process for resolution of racemic trans octahydro-1H-indole-2-carboxylic acid to obtain (2S,3aR,7aS) octahydro-1H-indole-2-carboxylic acid compound of formula (IV) preferably using R-(+)-phenyl ethyl amine as a resolving agent. A solvent comprising an alcohol, preferably ethanol, may be used in the resolution step. All the processes in the prior art describe resolving the esters of racemic trans octahydro-1H-indole-2-carboxylic acid; none of the prior art teaches a process for resolving trans octahydro-1H-indole-2-carboxylic acid.

During the process of optimizing the reaction conditions for the present invention, surprising results were obtained, which led to another object of the present invention. It was found that trandolapril can be synthesized by reacting NCA directly with racemic trans octahydro-1H-indole-2-carboxylic acid. There is no need to resolve the compound of formula (III). This leads to an efficient process.

Also, we have found that NCA reacts selectively with the desired isomer of trans octahydro-1H-indole-2-carboxylic acid (isomer D, above), thus making the process of the present invention a stereoselective process. The use of a water immiscible inert organic solvent during the condensation step contributes to the stereoselectivity of the process. The use of both a water immiscible inert organic solvent and a sub-molar proportion of the N-[1-(S)-ethoxy carbonyl-3-phenyl propyl]-L-alanine N-carboxyanhydride (II) relative to the trans octahydro-1H-indole-2-carboxylic acid (III) during the condensation step also contributes to the stereoselectivity.

It was observed that if NCA (II) was used in an equimolar proportion to the racemic trans acid, a significant amount of NCA remains unreacted and is recovered back as ECPPA. This led us to lower the amount of NCA (II) used in the reaction, which gave very encouraging results. Therefore, in the most preferred embodiment of the present invention, there is provided a process for synthesis of trandolapril comprising reaction of racemic trans octahydro-1H-indole-2-carboxylic acid with a sub-molar proportion of NCA (II), preferably about 0.4 to 0.9 moles more preferably 0.5 to 0.8 moles.

NCA required for the reaction was synthesized using known processes starting from N-[1-(S)-ethoxy carbonyl-3-phenyl propyl]-L-alanine.

The pharmaceutical composition of the present invention can be of any conventional form, such as a tablet, a pellet, a film-, sugar- or entero-coated tablet or pellet, a capsule, a suspension, a solution, an emulsion etc.

In formulating a pharmaceutical composition, the active ingredient can be combined with any conventional pharmaceutically acceptable carriers such as one or more pharmaceutically acceptable carriers selected from suitable vehicles, fillers, diluents, disintegrants, binding agents, colorants, surfactants, lubricants, preservatives, etc.

The following specific examples are presented to illustrate the best mode of carrying out the process of the present invention. The examples are not limited to the particular embodiments illustrated herein but include the permutations, which are set forth in the description.

EXAMPLES

Example 1

Step A: Preparation of N-[1-(S)-ethoxy carbonyl-3-phenyl propyl]-L-alanine N-carboxy anhydride (NCA)

Disodium dihydrogen phosphate dihydrate (177 gms; 0.994 moles) was dissolved in water (300 ml) at 35° C. and cooled to ambient temperature. Dichloromethane (250 ml) was charged and stirred for 15 mins. N-[1-(S)-ethoxy carbonyl-3-phenyl propyl]-L-alanine (106 gms; 0.381 moles) was added to the above solution and the reaction mass was cooled to 15° C. Solution of triphosgene (52.8 gms; 0.177 moles) dissolved dichloromethane (40 ml) was added dropwise to the reaction mass in 40 mins at 15-20° C. The reaction mass was further stirred for 30 min. Pyridine (0.5 ml; 0.006 moles) was added and the reaction mass was stirred for 1 hr at 15-20° C. The reaction mass was settled and layers were separated. Organic layer was washed with 2N HCl till the neutral pH obtained. The organic layer was further washed with water and dried over sodium sulphate. The solvent was evaporated to residue (110 gms).

Step B: Preparation of (2S,3aR,7aS)-1-[(2S)-2-[[(1S)-1-Ethoxycarbonyl-3-phenylpropyl]amino]-1-oxopropyl]octahydro-1H-indole-2-carboxylic acid (2S,3aR,7aS) octahydro-1H-indole-2-carboxylic acid (65 gms 0.384 moles) was stirred in dichloromethane (200 ml), triethyl amine (30 ml) was added under stirring at ambient temperature for 30 mins. N-[1-(S)-ethoxy carbonyl-3-phenyl propyl]-L-alanine N-carboxy anhydride (110 gms; 0.378 moles) (residue from Step A) dissolved in dichloromethane (50 ml) was added dropwise to the reaction mass at ambient temperature and further stirred for 3 hrs. Water (500 ml) was added and the reaction mass was cooled to 15° C., pH of the reaction mass was adjusted to 4.2 using 2N HCl. The organic layer was separated and aqueous layer reextracted with dichloromethane. The combined organic layer was dried with sodium sulphate and concentrated to residue. The residue was dissolved in ethylacetate at reflux temperature. The reaction mass was cooled to ambient temperature. The resulting solid was filtered and dried under vacuum to get 50 gms of Trandolapril (HPLC purity 99.5%)

Example 2

Racemic trans octahydro-1H-indole-2-carboxylic acid (65 gms; 0.384 moles) was stirred in dichloromethane (200 ml), triethyl amine (30 ml) was added under stirring at ambient temperature for 30 mins. N-[1-(S)ethoxy carbonyl-3-phenyl propyl]-L-alanine N-carboxyanhydride (67 gms; 0.23 moles) (prepared using procedure of Step A of Example 1) dissolved in dichloromethane 300 ml) was added dropwise to the reaction mass at ambient temperature and further stirred for 3 hrs. Water (500 ml) was added and the reaction mass was cooled to 15° C., pH of the reaction mass was adjusted to 4.2 using 2N HCl. The organic layer was separated. The organic layer was dried with sodium sulphate and concentrated to residue. The residue was dissolved in ethylacetate at reflux temperature. The reaction mass was cooled to ambient temperature. The resulting solid was filtered and dried under vacuum at 30-35° C. to get 34 gms of Trandolapril (HPLC purity 99.3%).

Example 3

Racemic trans octahydro-1H-indole-2-carboxylic acid (100 gms; 0.592 moles) was stirred in dichloromethane (300 ml), triethyl amine (46 ml) was added under stirring at ambient temperature for 30 mins. N-[1-(S)-ethoxy carbonyl-3-phenyl propyl]-L-alanine N-carboxyanhydride (119 gms; 0.42 moles) (prepared using procedure of Step A of Example 1) dissolved in dichloromethane (300 ml) was added dropwise to the reaction mass at ambient temperature and further stirred for 3 hrs. Water (700 ml) was added and the reaction mass was cooled to 15° C., pH of the reaction mass was adjusted to 4.2 using 2N HCl. The organic layer was separated. The organic layer was dried with sodium sulphate and concentrated to residue. The residue was dissolved in ethylacetate at reflux temperature. The reaction mass was cooled to ambient temperature. The resulting solid was filtered and dried under vacuum at 30-35° C. to get 55 gms of trandolapril (HPLC purity 99.5%).

Example 4

Racemic trans octahydro-1H-indole-2-carboxylic acid (50 gms; 0.295 moles) was stirred in dichloromethane (150 ml), triethyl amine (23 ml) was added under stirring at ambient temperature for 30 mins. N-[1-(S)-ethoxy carbonyl-3-phenyl propyl]-L-alanine N-carboxyanhydride (41 gms; 0.148 moles) (prepared using procedure of Step A of Example 1) dissolved in dichloromethane (150 ml) was added dropwise to the reaction mass at ambient temperature and further stirred for 3 hrs. Water (350 ml) was added and the reaction mass was cooled to 15° C., pH of the reaction mass was adjusted to 4.2 using 2N HCl. The organic layer was separated. The organic layer was dried with sodium sulphate and concentrated to residue. The residue was dissolved in ethylacetate at reflux temperature. The reaction mass was cooled to ambient temperature. The resulting solid was filtered and dried under vacuum at 30-35° C. to get 25 gms of trandolapril (HPLC purity 99.3%).

Example 5

Racemic trans octahydro-1H-indole-2-carboxylic acid (410 gms 2.42 moles) was refluxed in ethyl alcohol (3.8 ltrs). Heating of the reaction mass was discontinued, R-(+)-phenyl ethyl amine (500 gms; 4.13 moles) was charged to the reaction mass and stirred at ambient temp for 16-18 hrs. The reaction mass was then chilled to 10° C. and resulting solid was filtered. This solid was stirred in a mixture of water (3.6 ltrs.) and 10% NaOH (100 ml) for 15 mins. The clear aqueous layer was washed with ethyl acetate (1 ltr). The pH of the aqueous layer was adjusted to 6.5 using 10% HCl. The aqueous layer was concentrated under vacuum below 60° C. to residue. Acetonitrile (100 ml) was charged and distilled completely, further acetonitrile (100 ml) was charged and the resulting suspension was stirred at ambient temperature for 1 hr. and filtered. The solid was filtered and washed with acetonitrile and dried under vacuum at 60° C. to give 200 gms of (2S,3aR,7aS) octahydro-1H-indole-2-carboxylic acid.

It will be appreciated that the invention may be modified within the scope of the appended claims.

The invention claimed is:
1. A process for the synthesis of trandolapril of Formula (I)

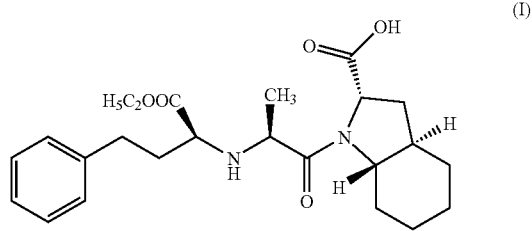

which comprises condensing N-[1-(S)-ethoxycarbonyl-3-phenylpropyl]-L-alanine carboxyanhydride compound of formula (II)

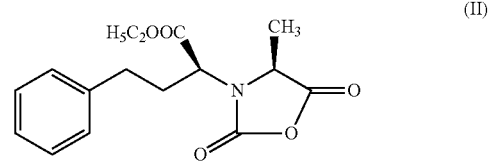

with trans octahydro-1H-indole-2-carboxylic acid of formula (III);

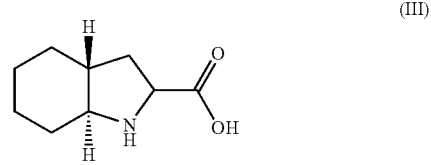

in a first organic solvent comprising a water immiscible inert organic solvent and in the presence of a base, and isolating trandolapril of formula (I) from a second organic solvent, wherein the N-[1-(S)-ethoxycarbonyl-3-phenylpropyl]-L-alanine N-carboxyanhydride compound of formula (II) is reacted in a sub-molar proportion relative to the trans octahydro-1H-indole-2-carboxylic acid of formula (III).

2. The process according to claim 1, wherein the molar ratio of N-[1-(S)-ethoxycarbonyl-3-phenylpropyl]-L-alanine N-carboxyanhydride compound of formula (II) to trans octahydro-1H-indole-2-carboxylic acid of formula (III) is 0.4-0.9:1.

3. The process according to claim 2, wherein the molar ratio of N-[1-(S)-ethoxycarbonyl-3-phenylpropyl]-L-alanine N-carboxyanhydride compound of formula (II) to trans octahydro-1H-indole-2-carboxylic acid of formula (III) is 0.5-0.8:1.

4. The process according to claim 1, wherein said first organic solvent is dichloromethane, dichloroethane, chloroform, toluene, xylene or an organic ester.

5. The process according to claim 1, wherein said first organic solvent is dichloromethane.

6. The process according to claim 1, wherein said base used for the condensation is an organic base.

7. The process according to claim 6, wherein said base is triethylamine.

8. The process according to claim 1, wherein said second organic solvent is ethyl acetate, isopropyl acetate, acetone, acetonitrile or isopropyl alcohol.

9. The process according to claim 1, wherein said second organic solvent is acetonitrile.

10. The process according to claim 1, further comprising quenching the product of the condensation reaction with water.

11. The process according to claim 10, further comprising adjusting the pH of the quenched product to 4 to 7 with an acid.

12. The process according to claim 11, wherein the pH is adjusted to 4.2.

13. The process according to claim 12, further comprising extracting the pH-adjusted product with a suitable solvent, followed by concentrating the extracted product to a residue.

14. The process according to claim 13, wherein the second organic solvent is used to isolate trandolapril from the residue.

* * * * *

UNITED STATES PATENT AND TRADEMARK OFFICE
CERTIFICATE OF CORRECTION

PATENT NO.        : 7,973,173 B2
APPLICATION NO.   : 11/993858
DATED             : July 5, 2011
INVENTOR(S)       : Rajendra Narayanrao Kankan et al.

It is certified that error appears in the above-identified patent and that said Letters Patent is hereby corrected as shown below:

IN THE CLAIMS:

Column 10, Claim 1, Line 27, replace "phenylpropyl]-L-alanine carboxyanhydride compound" with
-- phenylpropyl]-L-alanine N-carboxyanhydride compound --

Signed and Sealed this
Sixteenth Day of August, 2011

David J. Kappos
*Director of the United States Patent and Trademark Office*